United States Patent
Qian et al.

(10) Patent No.: US 10,464,972 B2
(45) Date of Patent: Nov. 5, 2019

(54) MULTIMER OF MUTANT PROTEIN A AND METHODS OF USING SAME

(71) Applicant: Nanjingjinsirui Science & Technology Biology Corp., Nanjing, Jiangsu (CN)

(72) Inventors: Hong Qian, Nanjing (CN); Tao Bai, Nanjing (CN); Rong Hua, Nanjing (CN)

(73) Assignee: Nanjingjinsirui Science & Technology Biology Corp., Nanjing, Jiangsu (CN)

( * ) Notice: Subject to any disclaimer, the term of this patent is extended or adjusted under 35 U.S.C. 154(b) by 0 days.

(21) Appl. No.: 16/169,376

(22) Filed: Oct. 24, 2018

(65) Prior Publication Data

US 2019/0048046 A1 Feb. 14, 2019

Related U.S. Application Data

(62) Division of application No. 14/778,395, filed as application No. PCT/CN2013/076445 on May 30, 2013.

(30) Foreign Application Priority Data

Mar. 18, 2013 (CN) .......................... 2013 1 0087284

(51) Int. Cl.
| | |
|---|---|
| *C12N 9/96* | (2006.01) |
| *C07K 14/31* | (2006.01) |
| *C07K 1/22* | (2006.01) |
| *C07K 16/00* | (2006.01) |
| *G01N 33/68* | (2006.01) |

(52) U.S. Cl.
CPC ................ *C07K 14/31* (2013.01); *C07K 1/22* (2013.01); *C07K 16/00* (2013.01); *G01N 33/6854* (2013.01); *C07K 2319/21* (2013.01); *C07K 2319/705* (2013.01)

(58) Field of Classification Search
None
See application file for complete search history.

(56) References Cited

U.S. PATENT DOCUMENTS

| | | | |
|---|---|---|---|
| 7,709,209 | B2 | 5/2010 | Hober et al. |
| 8,354,510 | B2 | 1/2013 | Hober et al. |
| 8,357,778 | B2 | 1/2013 | Sato |
| 8,772,447 | B2 | 7/2014 | Hall et al. |
| 2013/0096276 | A1 | 4/2013 | Yoshida et al. |
| 2016/0237124 | A1* | 8/2016 | Qian ........................ C07K 1/22 |

FOREIGN PATENT DOCUMENTS

| | | | |
|---|---|---|---|
| CN | 102516372 | A | 6/2012 |
| CN | 102844432 | A | 12/2012 |

OTHER PUBLICATIONS

Gulich, S., et al. "Stability towards alkaline conditions can be engineered into a protein ligand", Journal of biotechnology, 80 (2000) 169-178.
Gulich, S. et al Protein engineering of an IgG-binding domain allows milder elution conditions during affinity chromatography. J. of Bio. 76 (2000) 233-244.
Hober, S. et al. "Protein A chromatography for antibody purification", Journal of Chromatography B, 848 (2007) 40-47.
Linhult, M. et al. "Affinity ligands for industrial protein purification," Protein and Peptide Letters, (2005), 12, 305-310.
Lund, L et al. "Exploring variation in binding of Protein A and Protein G to immunoglobulin type G by isothermal titration calorimetry," Journal of Molecular Recognition (2011), 24, 945-952.
Magdeldin, S. and Moser, A., "Affinity Chromatography: Principles and Applications", Intechopen, 2012.
Minakuchi, K. et al. "Remarkable alkaline stability of an engineered protein A as immunoglobulin affinity ligand: C domain having only one amino acid substitution" Protein Science, 22 (2013), 1230-1238.
Yu, F., et al. "Tailor-making a protein A-derived domain for efficient site-specific photocoupling to Fc of mouse IgG1" PLoS ONE, 8 (2013), e56597.
Heu, W., et al, "Protein binder for affinity purification of human immunoglobulin antibodies" Analytical Chemistry, 2014.
Yang, L., et al. "Effect of cleaning agents and additives on Protein A ligand degredation and chromatography performance", Journal of Chromatography A, (2015) 1385, 63-68.
Huang, B., et al. "Molecular mechanism of the affinity interactions between protein A and human immunoglobulin G1 revealed by molecular simulations", Journal of Physical Chemistry, (2011) 115, 4168-4176.
Huang B. et al. "Molecular mechanism of the effects of salt and pH on the affinity between protein A and human immunoglobulin G1 revealed by molecular simulations", Journal of Physical Chemistry, (2012) 116, 424-433.

(Continued)

*Primary Examiner* — Hope A Robinson
(74) *Attorney, Agent, or Firm* — Panitch Schwarze Belisario & Nadel LLP

(57) ABSTRACT

A series of protein A mutants having high alkali resistance, and methods of using the protein A mutants are provided. The protein A mutants have a high binding affinity for regions of immunoglobulin proteins other than the complementarity determining regions. The protein A mutants can be coupled to a solid support for immunoglobulin isolation, or conjugated to a label for immunoglobulin detection. This series of protein A mutants have high chemical stability under alkaline conditions of pH 13-14, and can also be used as chromatography ligands for purification procedures that use alkaline solutions under harsh conditions, such as Clean-In-Place (CIP). Also provided are methods of immunoglobulin separation and purification, and alkali regeneration of affinity chromatography medium that uses protein A as a ligand.

8 Claims, 4 Drawing Sheets

Specification includes a Sequence Listing.

(56) References Cited

OTHER PUBLICATIONS

Salvalaglio, M., "Molecular modeling of protein A affinity chromatography", Journal of Chromatography A, (2009) 1216, 8678-8686.
Linhult, M., et al. "Improving the tolerance of a protein A analogue to repeated alkaline exposures using a bypass mutagenesis approach", Proteins: Structure, Function, and bioinformatics, 55 (2004), 407-416.
Jiang, C., et al. "A mechanistic study of Protein A chromatography resin lifetime", Journal of Chromatography A, (2009) 1216, 5849-5855.
Xia, H., et al. "Molecular Modification of Protein A to Improve the Elution pH and Alaki Resistance in Affinity Chromatography", Applied Biochemistry and Biotechnology, 172 (2014), 4002-4012.
International Search Report dated Dec. 26, 2013 in corresponding PCT/CN2013/076445.
Hjerten, S., "The preparation of agarose spheres for chomatography of molecules and particles", Biochimica et Biophysica Acta, 79 (1964) 393-398. (Abstract Only).
Brown, N.L. et al., "A study of the interactions between an IgG-binding domain based on the B domain of staphylococcal protein A and rabbit IgG" Molecular Biotechnology, 10 (1998), 9-16. (Abstract Only).
Written Opinion dated Dec. 26, 2013 in PCT/CN2013/076445.

\* cited by examiner

```
                          SEQUENCE LISTING

<160> NUMBER OF SEQ ID NOS: 56

<210> SEQ ID NO 1
<211> LENGTH: 58
<212> TYPE: PRT
<213> ORGANISM: Artificial Sequence
<220> FEATURE:
<223> OTHER INFORMATION: Protein A1 mutant sequence

<400> SEQUENCE: 1

Ala Asp Gly Lys Phe Glu Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Gln Ser Thr Asn Val Leu Gly Glu Ala
        35                  40                  45

Lys Lys Leu Asn Asp Ala Gln Ala Pro Lys
    50                  55

<210> SEQ ID NO 2
<211> LENGTH: 58
<212> TYPE: PRT
<213> ORGANISM: Artificial Sequence
<220> FEATURE:
<223> OTHER INFORMATION: Protein A2 mutant sequence

<400> SEQUENCE: 2

Ala Asp Gly Lys Phe Glu Lys Glu Gln Gln Asn Ala Phe Tyr Glu Ile
1               5                   10                  15

Leu His Leu Pro Asn Leu Thr Glu Glu Gln Arg Asn Ala Phe Ile Lys
            20                  25                  30

Ser Ile Arg Asp Asp Pro Ser Gln Ser Thr Asn Val Leu Gly Glu Ala
        35                  40                  45

Lys Lys Leu Asn Asp Ala Gln Ala Pro Lys
    50                  55

<210> SEQ ID NO 3
<211> LENGTH: 70
<212> TYPE: PRT
<213> ORGANISM: Artificial Sequence
<220> FEATURE:
<223> OTHER INFORMATION: protein A1 sequence with N-terminal 6X-
      histidine tag

<400> SEQUENCE: 3

Met Gly Ser His His His His His His Gly Ser Gly Ala Asp Gly Lys
1               5                   10                  15

Phe Glu Lys Glu Gln Gln Asn Ala Phe Tyr Glu Ile Leu His Leu Pro
            20                  25                  30
```

```
Asn Leu Thr Glu Glu Gln Arg Asn Ala Phe Ile Gln Ser Leu Lys Asp
            35                  40                  45

Asp Pro Ser Gln Ser Thr Asn Val Leu Gly Glu Ala Lys Lys Leu Asn
        50                  55                  60

Asp Ala Gln Ala Pro Lys
65                  70

<210> SEQ ID NO 4
<211> LENGTH: 221
<212> TYPE: DNA
<213> ORGANISM: Artificial Sequence
<220> FEATURE:
<223> OTHER INFORMATION: gene encoding protein A1 sequence with N-
      terminal 6X-histidine tag

<400> SEQUENCE: 4
ccatgggctc acatcatcat catcatcacg gctcgggtgc ggacggtaaa tttgaaaaag      60
aacagcagaa tgcgttctac gaaattctgc atctgccgaa cctgaccgaa gaacagcgta    120
atgcatttat ccagtctctg aaagatgatc cgagccagtc tacgaacgtg ctgggtgaag    180
cgaaaaaact gaacgatgcg caggccccga atgacatat g                         221

<210> SEQ ID NO 5
<211> LENGTH: 70
<212> TYPE: PRT
<213> ORGANISM: Artificial Sequence
<220> FEATURE:
<223> OTHER INFORMATION: protein A2 sequence with N-terminal 6X-
      histidine tag

<400> SEQUENCE: 5

Met Gly Ser His His His His His His Gly Ser Gly Ala Asp Gly Lys
1               5                  10                  15

Phe Glu Lys Glu Gln Gln Asn Ala Phe Tyr Glu Ile Leu His Leu Pro
            20                  25                  30

Asn Leu Thr Glu Glu Gln Arg Asn Ala Phe Ile Lys Ser Ile Arg Asp
            35                  40                  45

Asp Pro Ser Gln Ser Thr Asn Val Leu Gly Glu Ala Lys Lys Leu Asn
        50                  55                  60

Asp Ala Gln Ala Pro Lys
65                  70

<210> SEQ ID NO 6
<211> LENGTH: 221
<212> TYPE: DNA
<213> ORGANISM: Artificial Sequence
<220> FEATURE:
<223> OTHER INFORMATION: gene encoding protein A2 sequence with N-
      terminal 6X-histidine tag

<400> SEQUENCE: 6
ccatgggctc gcaccaccac caccaccacg gctcgggcgc agatggcaag tttgaaaaag      60
aacaacagaa cgcattctac gaaatcctgc atctgccgaa cctgaccgaa gaacagcgta    120
acgcattcat caagtctatc cgcgatgatc cgagccagtc tacgaacgtg ctgggcgaag    180
cgaaaaaact gaatgatgcg caggccccga atgacatat g                         221

<210> SEQ ID NO 7
<211> LENGTH: 50
<212> TYPE: DNA
<213> ORGANISM: Artificial Sequence
<220> FEATURE:
```

<223> OTHER INFORMATION: Primer 7 sequence

<400> SEQUENCE: 7
aactttaaga aggagatata ccatgggctc acatcatcat catcatcacg         50

<210> SEQ ID NO 8
<211> LENGTH: 50
<212> TYPE: DNA
<213> ORGANISM: Artificial Sequence
<220> FEATURE:
<223> OTHER INFORMATION: primer 8 sequence

<400> SEQUENCE: 8
ttagcagccg gatcctcgag catatgtcat ttcggggcct gcgcatcatt         50

<210> SEQ ID NO 9
<211> LENGTH: 50
<212> TYPE: DNA
<213> ORGANISM: Artificial Sequence
<220> FEATURE:
<223> OTHER INFORMATION: primer 9 sequence

<400> SEQUENCE: 9
ttagcagccg gatcctcgag catatgtcat ttcggggcct gcgcatcgtt         50

<210> SEQ ID NO 10
<211> LENGTH: 128
<212> TYPE: PRT
<213> ORGANISM: Artificial Sequence
<220> FEATURE:
<223> OTHER INFORMATION: protein AA1 dimer sequence with N-terminal 6X-
       histidine tag

<400> SEQUENCE: 10

Met Gly Ser His His His His His His Gly Ser Gly Ala Asp Gly Lys
1               5                   10                  15

Phe Glu Lys Glu Gln Gln Asn Ala Phe Tyr Glu Ile Leu His Leu Pro
            20                  25                  30

Asn Leu Thr Glu Glu Gln Arg Asn Ala Phe Ile Gln Ser Leu Lys Asp
        35                  40                  45

Asp Pro Ser Gln Ser Thr Asn Val Leu Gly Glu Ala Lys Lys Leu Asn
    50                  55                  60

Asp Ala Gln Ala Pro Lys Ala Asp Gly Lys Phe Glu Lys Glu Gln Gln
65                  70                  75                  80

Asn Ala Phe Tyr Glu Ile Leu His Leu Pro Asn Leu Thr Glu Glu Gln
                85                  90                  95

Arg Asn Ala Phe Ile Gln Ser Leu Lys Asp Asp Pro Ser Gln Ser Thr
            100                 105                 110

Asn Val Leu Gly Glu Ala Lys Lys Leu Asn Asp Ala Gln Ala Pro Lys
        115                 120                 125

<210> SEQ ID NO 11
<211> LENGTH: 395
<212> TYPE: DNA
<213> ORGANISM: Artificial Sequence
<220> FEATURE:
<223> OTHER INFORMATION: gene encoding protein AA1 dimer sequence with
       N-terminal 6X-histidine tag

<400> SEQUENCE: 11
ccatgggctc acatcatcat catcatcacg gctcgggtgc ggacggtaaa tttgaaaaag    60
aacagcagaa tgcgttctac gaaattctgc atctgccgaa cctgaccgaa gaacagcgta   120

```
atgcatttat ccagtctctg aaagatgatc cgagccagtc tacgaacgtg ctgggtgaag    180
cgaaaaaact gaacgatgcg caggccccga agcggatgg caaattcgaa aagaacagc     240 agaacgcctt ctatgaaatt ctgcacctgc cgaatctgac ggaagaacag cgcaatgcgt   300
tcatccagag cctgaaagac gatccgagcc agtccacgaa tgttctgggc gaagcgaaaa   360
aactgaatga cgcacaagca ccgaaatgac atatg                              395
```

<210> SEQ ID NO 12
<211> LENGTH: 128
<212> TYPE: PRT
<213> ORGANISM: Artificial Sequence
<220> FEATURE:
<223> OTHER INFORMATION: protein AA2 dimer sequence with N-terminal 6X-
      histidine tag

<400> SEQUENCE: 12

```
Met Gly Ser His His His His His His Gly Ser Gly Ala Asp Gly Lys
1               5                   10                  15

Phe Glu Lys Glu Gln Gln Asn Ala Phe Tyr Glu Ile Leu His Leu Pro
                20                  25                  30

Asn Leu Thr Glu Glu Gln Arg Asn Ala Phe Ile Lys Ser Ile Arg Asp
            35                  40                  45

Asp Pro Ser Gln Ser Thr Asn Val Leu Gly Glu Ala Lys Lys Leu Asn
        50                  55                  60

Asp Ala Gln Ala Pro Lys Ala Asp Gly Lys Phe Glu Lys Glu Gln Gln
65                  70                  75                  80

Asn Ala Phe Tyr Glu Ile Leu His Leu Pro Asn Leu Thr Glu Glu Gln
                85                  90                  95

Arg Asn Ala Phe Ile Lys Ser Ile Arg Asp Asp Pro Ser Gln Ser Thr
            100                 105                 110

Asn Val Leu Gly Glu Ala Lys Lys Leu Asn Asp Ala Gln Ala Pro Lys
        115                 120                 125
```

<210> SEQ ID NO 13
<211> LENGTH: 395
<212> TYPE: DNA
<213> ORGANISM: Artificial Sequence
<220> FEATURE:
<223> OTHER INFORMATION: gene encoding protein AA2 dimer sequence with
      N-terminal 6X-histidine tag

<400> SEQUENCE: 13

```
ccatgggctc gcaccaccac caccaccacg gctcgggcgc agatggcaag tttgaaaaag    60
aacaacagaa cgcattctac gaaatcctgc atctgccgaa cctgaccgaa gaacagcgta   120
acgcattcat caagtctatc cgcgatgatc cgagccagtc tacgaacgtg ctgggcgaag   180
cgaaaaaact gaatgatgcg caggccccga agcggatgg taaatttgaa aagaacagc    240 agaacgcctt ctatgaaatt ctgcacctgc cgaatctgac ggaagaacag cgtaatgcgt   300
tcattaaaag cattcgtgac gatccgagcc agagcacgaa tgtcctgggc gaagccaaaa   360
aactgaacga cgcacaagca ccgaaatgac atatg                              395
```

<210> SEQ ID NO 14
<211> LENGTH: 50
<212> TYPE: DNA
<213> ORGANISM: Artificial Sequence
<220> FEATURE:
<223> OTHER INFORMATION: primer 14 sequence

<400> SEQUENCE: 14
ttagcagccg atcctcgag catatgtcat tcggtgctt gtgcgtcatt          50

<210> SEQ ID NO 15
<211> LENGTH: 50
<212> TYPE: DNA
<213> ORGANISM: Artificial Sequence
<220> FEATURE:
<223> OTHER INFORMATION: primer 15 sequence

<400> SEQUENCE: 15
ttagcagccg atcctcgag catatgtcat tcggtgctt gtgcgtcgtt          50

<210> SEQ ID NO 16
<211> LENGTH: 49
<212> TYPE: DNA
<213> ORGANISM: Artificial Sequence
<220> FEATURE:
<223> OTHER INFORMATION: primer 4-1 sequence

<400> SEQUENCE: 16
ccatgggctc acatcatcat catcatcacg gctcgggtgc ggacggtaa         49

<210> SEQ ID NO 17
<211> LENGTH: 41
<212> TYPE: DNA
<213> ORGANISM: Artificial Sequence
<220> FEATURE:
<223> OTHER INFORMATION: primer 4-2 sequence

<400> SEQUENCE: 17
acgcattctg ctgttctttt tcaaatttac cgtccgcacc c                 41

<210> SEQ ID NO 18
<211> LENGTH: 41
<212> TYPE: DNA
<213> ORGANISM: Artificial Sequence
<220> FEATURE:
<223> OTHER INFORMATION: primer 4-3 sequence

<400> SEQUENCE: 18
agaacagcag aatgcgttct acgaaattct gcatctgccg a                 41

<210> SEQ ID NO 19
<211> LENGTH: 41
<212> TYPE: DNA
<213> ORGANISM: Artificial Sequence
<220> FEATURE:
<223> OTHER INFORMATION: primer 4-4 sequence

<400> SEQUENCE: 19 cattcgctg ttcttcggtc aggttcggca gatgcagaat t                  41

<210> SEQ ID NO 20
<211> LENGTH: 50
<212> TYPE: DNA
<213> ORGANISM: Artificial Sequence
<220> FEATURE:
<223> OTHER INFORMATION: primer 4-5 sequence

<400> SEQUENCE: 20
ccgaagaaca gcgtaatgca tttatccagt ctctgaaaga tgatccgagc        50

<210> SEQ ID NO 21
<211> LENGTH: 40

<210> SEQ ID NO 21
<211> LENGTH: 40
<212> TYPE: DNA
<213> ORGANISM: Artificial Sequence
<220> FEATURE:
<223> OTHER INFORMATION: primer 4-6 sequence

<400> SEQUENCE: 21
acccagcacg ttcgtagact ggctcggatc atctttcaga                                40

<210> SEQ ID NO 22
<211> LENGTH: 40
<212> TYPE: DNA
<213> ORGANISM: Artificial Sequence
<220> FEATURE:
<223> OTHER INFORMATION: primer 4-7 sequence

<400> SEQUENCE: 22
tacgaacgtg ctgggtgaag cgaaaaaact gaacgatgcg                                40

<210> SEQ ID NO 23
<211> LENGTH: 40
<212> TYPE: DNA
<213> ORGANISM: Artificial Sequence
<220> FEATURE:
<223> OTHER INFORMATION: primer 4-8 sequence

<400> SEQUENCE: 23
catatgtcat ttcggggcct gcgcatcgtt cagtttttc                                 40

<210> SEQ ID NO 24
<211> LENGTH: 50
<212> TYPE: DNA
<213> ORGANISM: Artificial Sequence
<220> FEATURE:
<223> OTHER INFORMATION: primer 6-1 sequence

<400> SEQUENCE: 24
ccatgggctc gcaccaccac caccaccacg gctcgggcgc agatggcaag                     50

<210> SEQ ID NO 25
<211> LENGTH: 40
<212> TYPE: DNA
<213> ORGANISM: Artificial Sequence
<220> FEATURE:
<223> OTHER INFORMATION: primer 6-2 sequence

<400> SEQUENCE: 25
atgcgttctg ttgttctttt tcaaacttgc catctgcgcc                                40

<210> SEQ ID NO 26
<211> LENGTH: 43
<212> TYPE: DNA
<213> ORGANISM: Artificial Sequence
<220> FEATURE:
<223> OTHER INFORMATION: primer 6-3 sequence

<400> SEQUENCE: 26
aaagaacaac agaacgcatt ctacgaaatc ctgcatctgc cga                            43

<210> SEQ ID NO 27
<211> LENGTH: 41
<212> TYPE: DNA
<213> ORGANISM: Artificial Sequence
<220> FEATURE:
<223> OTHER INFORMATION: primer 6-4 sequence

<400> SEQUENCE: 27
tgcgttacgc tgttcttcgg tcaggttcgg cagatgcagg a    41

<210> SEQ ID NO 28
<211> LENGTH: 43
<212> TYPE: DNA
<213> ORGANISM: Artificial Sequence
<220> FEATURE:
<223> OTHER INFORMATION: primer 6-5 sequence

<400> SEQUENCE: 28
agaacagcgt aacgcattca tcaagtctat ccgcgatgat ccg    43

<210> SEQ ID NO 29
<211> LENGTH: 40
<212> TYPE: DNA
<213> ORGANISM: Artificial Sequence
<220> FEATURE:
<223> OTHER INFORMATION: primer 6-6 sequence

<400> SEQUENCE: 29
cccagcacgt tcgtagactg gctcggatca tcgcggatag    40

<210> SEQ ID NO 30
<211> LENGTH: 40
<212> TYPE: DNA
<213> ORGANISM: Artificial Sequence
<220> FEATURE:
<223> OTHER INFORMATION: primer 6-7 sequence

<400> SEQUENCE: 30
ctacgaacgt gctgggcgaa gcgaaaaaac tgaatgatgc    40

<210> SEQ ID NO 31
<211> LENGTH: 42
<212> TYPE: DNA
<213> ORGANISM: Artificial Sequence
<220> FEATURE:
<223> OTHER INFORMATION: primer 6-8 sequence

<400> SEQUENCE: 31
catatgtcat ttcggggcct gcgcatcatt cagttttttc gc    42

<210> SEQ ID NO 32
<211> LENGTH: 49
<212> TYPE: DNA
<213> ORGANISM: Artificial Sequence
<220> FEATURE:
<223> OTHER INFORMATION: primer 11-1 sequence

<400> SEQUENCE: 32
ccatgggctc acatcatcat catcatcacg gctcgggtgc ggacggtaa    49

<210> SEQ ID NO 33
<211> LENGTH: 41
<212> TYPE: DNA
<213> ORGANISM: Artificial Sequence
<220> FEATURE:
<223> OTHER INFORMATION: primer 11-2 sequence

<400> SEQUENCE: 33
acgcattctg ctgttctttt tcaaatttac cgtccgcacc c    41

<210> SEQ ID NO 34
<211> LENGTH: 49
<212> TYPE: DNA
<213> ORGANISM: Artificial Sequence -continued

```
<220> FEATURE:
<223> OTHER INFORMATION: primer 11-3 sequence

<400> SEQUENCE: 34
agaacagcag aatgcgttct acgaaattct gcatctgccg aacctgacc            49

<210> SEQ ID NO 35
<211> LENGTH: 49
<212> TYPE: DNA
<213> ORGANISM: Artificial Sequence
<220> FEATURE:
<223> OTHER INFORMATION: primer 11-4 sequence

<400> SEQUENCE: 35
tcagagactg gataaatgca ttacgctgtt cttcggtcag gttcggcag            49

<210> SEQ ID NO 36
<211> LENGTH: 50
<212> TYPE: DNA
<213> ORGANISM: Artificial Sequence
<220> FEATURE:
<223> OTHER INFORMATION: primer 11-5 sequence

<400> SEQUENCE: 36
tgcatttatc cagtctctga aagatgatcc gagccagtct acgaacgtgc            50

<210> SEQ ID NO 37
<211> LENGTH: 50
<212> TYPE: DNA
<213> ORGANISM: Artificial Sequence
<220> FEATURE:
<223> OTHER INFORMATION: primer 11-6 sequence

<400> SEQUENCE: 37
cctgcgcatc gttcagtttt ttcgcttcac ccagcacgtt cgtagactgg            50

<210> SEQ ID NO 38
<211> LENGTH: 45
<212> TYPE: DNA
<213> ORGANISM: Artificial Sequence
<220> FEATURE:
<223> OTHER INFORMATION: primer 11-7 sequence

<400> SEQUENCE: 38
tgaacgatgc gcaggccccg aaagcggatg gcaaattcga aaaag                45

<210> SEQ ID NO 39
<211> LENGTH: 50
<212> TYPE: DNA
<213> ORGANISM: Artificial Sequence
<220> FEATURE:
<223> OTHER INFORMATION: primer 11-8 sequence

<400> SEQUENCE: 39
gcagaatttc atagaaggcg ttctgctgtt cttttcgaa tttgccatcc             50

<210> SEQ ID NO 40
<211> LENGTH: 50
<212> TYPE: DNA
<213> ORGANISM: Artificial Sequence
<220> FEATURE:
<223> OTHER INFORMATION: primer 11-9 sequence

<400> SEQUENCE: 40
cgccttctat gaaattctgc acctgccgaa tctgacggaa gaacagcgca            50
```

<210> SEQ ID NO 41
<211> LENGTH: 50
<212> TYPE: DNA
<213> ORGANISM: Artificial Sequence
<220> FEATURE:
<223> OTHER INFORMATION: primer 11-10 sequence

<400> SEQUENCE: 41
gctcggatcg tctttcaggc tctggatgaa cgcattgcgc tgttcttccg          50

<210> SEQ ID NO 42
<211> LENGTH: 49
<212> TYPE: DNA
<213> ORGANISM: Artificial Sequence
<220> FEATURE:
<223> OTHER INFORMATION: primer 11-11 sequence

<400> SEQUENCE: 42
tgaaagacga tccgagccag tccacgaatg ttctgggcga agcgaaaaa           49

<210> SEQ ID NO 43
<211> LENGTH: 50
<212> TYPE: DNA
<213> ORGANISM: Artificial Sequence
<220> FEATURE:
<223> OTHER INFORMATION: primer 11-12 sequence

<400> SEQUENCE: 43
catatgtcat ttcggtgctt gtgcgtcatt cagttttttc gcttcgccca          50

<210> SEQ ID NO 44
<211> LENGTH: 50
<212> TYPE: DNA
<213> ORGANISM: Artificial Sequence
<220> FEATURE:
<223> OTHER INFORMATION: primer 13-1 sequence

<400> SEQUENCE: 44
ccatgggctc gcaccaccac caccaccacg gctcgggcgc agatggcaag          50

<210> SEQ ID NO 45
<211> LENGTH: 47
<212> TYPE: DNA
<213> ORGANISM: Artificial Sequence
<220> FEATURE:
<223> OTHER INFORMATION: primer 13-2 sequence

<400> SEQUENCE: 45
tcgtagaatg cgttctgttg ttcttttttca aacttgccat ctgcgcc           47

<210> SEQ ID NO 46
<211> LENGTH: 45
<212> TYPE: DNA
<213> ORGANISM: Artificial Sequence
<220> FEATURE:
<223> OTHER INFORMATION: primer 13-3 sequence

<400> SEQUENCE: 46
acagaacgca ttctacgaaa tcctgcatct gccgaacctg accga              45

<210> SEQ ID NO 47
<211> LENGTH: 50
<212> TYPE: DNA
<213> ORGANISM: Artificial Sequence
<220> FEATURE:
<223> OTHER INFORMATION: primer 13-4 sequence

```
<400> SEQUENCE: 47
cgcggataga cttgatgaat gcgttacgct gttcttcggt caggttcggc           50

<210> SEQ ID NO 48
<211> LENGTH: 49
<212> TYPE: DNA
<213> ORGANISM: Artificial Sequence
<220> FEATURE:
<223> OTHER INFORMATION: primer 13-5 sequence

<400> SEQUENCE: 48
tcatcaagtc tatccgcgat gatccgagcc agtctacgaa cgtgctggg            49

<210> SEQ ID NO 49
<211> LENGTH: 47
<212> TYPE: DNA
<213> ORGANISM: Artificial Sequence
<220> FEATURE:
<223> OTHER INFORMATION: primer 13-6 sequence

<400> SEQUENCE: 49
ggcctgcgca tcattcagtt ttttcgcttc gcccagcacg ttcgtag              47

<210> SEQ ID NO 50
<211> LENGTH: 50
<212> TYPE: DNA
<213> ORGANISM: Artificial Sequence
<220> FEATURE:
<223> OTHER INFORMATION: primer 13-7 sequence

<400> SEQUENCE: 50
aatgatgcgc aggccccgaa agcggatggt aaatttgaaa agaacagca           50

<210> SEQ ID NO 51
<211> LENGTH: 50
<212> TYPE: DNA
<213> ORGANISM: Artificial Sequence
<220> FEATURE:
<223> OTHER INFORMATION: primer 13-8 sequence

<400> SEQUENCE: 51
aggtgcagaa tttcatagaa ggcgttctgc tgttcttttt caaatttacc          50

<210> SEQ ID NO 52
<211> LENGTH: 50
<212> TYPE: DNA
<213> ORGANISM: Artificial Sequence
<220> FEATURE:
<223> OTHER INFORMATION: primer 13-9 sequence

<400> SEQUENCE: 52
cttctatgaa attctgcacc tgccgaatct gacggaagaa cagcgtaatg          50

<210> SEQ ID NO 53
<211> LENGTH: 50
<212> TYPE: DNA
<213> ORGANISM: Artificial Sequence
<220> FEATURE:
<223> OTHER INFORMATION: primer 13-10 sequence

<400> SEQUENCE: 53
gctcggatcg tcacgaatgc ttttaatgaa cgcattacgc tgttcttccg          50

<210> SEQ ID NO 54
```

```
<211> LENGTH: 47
<212> TYPE: DNA
<213> ORGANISM: Artificial Sequence
<220> FEATURE:
<223> OTHER INFORMATION: primer 13-11 sequence

<400> SEQUENCE: 54
cgtgacgatc cgagccagag cacgaatgtc ctgggcgaag ccaaaaa            47

<210> SEQ ID NO 55
<211> LENGTH: 50
<212> TYPE: DNA
<213> ORGANISM: Artificial Sequence
<220> FEATURE:
<223> OTHER INFORMATION: primer 13-12 sequence

<400> SEQUENCE: 55
catatgtcat ttcggtgctt gtgcgtcgtt cagtttttg gcttcgccca          50

<210> SEQ ID NO 56
<211> LENGTH: 4
<212> TYPE: PRT
<213> ORGANISM: Artificial Sequence
<220> FEATURE:
<223> OTHER INFORMATION: exemplary linker sequence for protein A
      multimer

<400> SEQUENCE: 56

Ala Asp Gly Lys
1
```

MULTIMER OF MUTANT PROTEIN A AND METHODS OF USING SAME

CROSS-REFERENCE TO RELATED APPLICATION

This application is a divisional application of U.S. patent application Ser. No. 14/778,395, filed Sep. 18, 2015, now allowed, which is a Section 371 of International Application No. PCT/CN2013/076445, filed May 30, 2013, which was published in the Chinese language on Sep. 25, 2014 under International Publication No. WO 2014/146350 A1, the disclosures of which are herein incorporated by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "688096-79U1 Sequence Listing", creation date of Nov. 9, 2015, and having a size of 17 kb. The sequence listing submitted via EFS-Web is part of the specification and is herein incorporated by reference in its entirety.

FIELD OF THE INVENTION

The invention belongs to the field of protein engineering, relates to a series of Staphylococcal protein A mutants with high alkali resistance and their application.

BACKGROUND OF THE INVENTION

Biotechnology is one of the fastest growing high-tech fields in the world. As one of the hot spots, antibody drug development continues to improve the health and the life quality of many patients and has achieved remarkable market performance in recent years. Although investments in research and development of new drugs have been increased continuously, the number of innovative drugs that reach the market has dramatically decreased, and many small molecule drugs face the threat of the patent cliff. Therefore, in order to seek new growing points, many pharmaceutical companies are entering the field of antibody drug development. Currently, antibody drugs are widely used in basic biomedical research, diagnosis and treatment of diseases such as cancers, organ transplant rejection and autoimmune diseases.

In recent years, as a large number of therapeutic antibody drugs have been invented and used in the medical field, the production process draws a lot of attention from people. In general, large-scaled economic production of antibody drugs and diagnostic reagents are produced by cell culture at the intracellular level or secreted into the culture medium. The cell culturing process requires a culture medium supplemented with sugars, amino acids, and certain growth factors.

Therefore antibody must be isolated from culture medium as well as other cellular components and purified to a certain level before it can be used as a human therapeutic agent. Currently the most widely used method for antibody purification is affinity chromatography which is simple, fast and highly selective. With those advantages, affinity chromatography significantly reduces the subsequent steps of purification to save time and cost with no sacrifice of purity. Cost control is very important in the modern industrial production processes. If chromatography medium could be used repeatedly, it would significantly reduce the production cost of an antibody. However, previously used chromatography medium may retain un-eluted proteins, protein aggregates, or residual substances that could be harmful, such as viruses or endotoxins. So it is very critical that the previously used media must be cleaned before reusing. The most effective way to clean chromatography medium is Clean-In-Place (CIP) using alkaline solutions. The method involves a treatment with a buffer or solution containing 0.5M Sodium Hydroxide (NaOH). Using this rigorous clean method, impurities can be effectively removed from the medium, however, it may also damage the chromatography medium itself. Therefore, Protein A molecules with high alkali resistance which bind immunoglobulin as described in the present invention can be used as effective ligands for the purification of antibodies. Importantly, the chromatography medium can be treated by CIP with alkali solution and regenerated for repetitive use.

BRIEF SUMMARY OF THE INVENTION

This invention aims to address the disadvantages of existing technology and provide a specific series of mutations to the Protein A molecule which enable it high alkali resistance.

Another objective of the present invention is to provide applications of this protein A molecule.

The objective of this invention can be achieved by the following technical solutions:

A series of Protein A mutants of which the amino acid sequences are defined by SEQ ID NO:1 or SEQ ID NO:2, or defined by the amino acid sequences within immunoglobulin binding region that have more than 99% homology to the sequences defined by SEQ ID NO:1 or SEQ ID NO:2. Here immunoglobulin binding region is defined from the 7th amino acid residue to the 54th. of SEQ ID NO: 1 or SEQ ID NO:2.

Nucleic Acids Encoding the Protein A.

The present invention relates to protein A which is essentially a series of immunoglobulin-binding molecules which can tightly bind with immunoglobulin at regions other than the complementarity determining region, and at the meantime can withstand an alkali condition of pH13-14. Such an immunoglobulin binding protein A is composed of three α helical regions, which fold into a three-helix bundle structure. Protein A binds to the Fc part of an immunoglobulin through the residues on the helix 1 and 2 surface. Also Protein A has lower affinity toward the Fab part of an immunoglobulin, through the residues on the surface of helix 2 and 3. The residues in the center of the three-helix bundle form an hydrophobic core, of which the hydrophobic interactions could enable the high thermal stability of protein A.

Different from other types of non-alkali resistant Protein A, when the alkali resistant protein A species are placed in an alkaline environment of pH13-14, even though the hydrogen bonds which help to maintain the protein tertiary structure disappeared and all three α helixes would be stretched, the strong hydrophobic interactions among three helixes would still enforce α helix 1, 2 3 to stay closely to each other and to ensure their relative positions do not change significantly. Once the pH are brought back to a neutral environment, such as pH7-8, hydrogen bonds among α helix 1, 2, 3 would be recovered, then the overall conformation or tertiary structure of the tri-helix bundle could be restored to the one before alkali treatment. While other non-alkali resistant proteins are not able to restore their tertiary structures due to the lacking of this kind of hydrophobic core to maintain their structure. After being placed in an alkaline environment, like pH13-14, the structure of non-alkali resistant proteins would be completely destroyed, so when they are put back into a neutral environment like pH 7-8, the overall conformation or tertiary structure of the protein could not be restored to the one before alkali treatment. With this alkali resistance characteristics, monomeric Protein A or multimeric protein A coupled to a solid phase support which can be used for the isolation and purification purpose of an immunoglobulin molecule, or they can be also used for detection of immunoglobulin molecules by conjugating a marker or label. If these alkali resistant protein A are used as ligands for chromatography medium, the chromatography medium can be cleaned and regenerated by Clean-In-Place (CIP) with alkaline solutions.

As described in the invention, the molecular weight of the protein A monomer is around 6KD, composed of 58 amino acids, which can be chemically synthesized or recombinantly expressed. If recombinantly expressed, cell strains must be constructed firstly to carry a gene that encodes the amino acid sequence of the protein. Therefore, the following steps of procedure are required: first, obtain the protein A gene encoding the amino acid sequence by gene synthesis; second, insert the protein A gene into an expression vector. Here tags for purification or labels for identification can be inserted into the expression vectors as needed. And then transform the vector into a suitable cell line for further expression. By doing this, protein A (including monomeric or polymeric) which have immunoglobulin molecule binding affinity could be obtained from culture medium or cells. It should be noticed that the expression of protein A needs to be tightly controlled. So selecting vectors for the expression of protein A is very important, and those vectors should have the following features: 1) an expression vector should have a promoter or transcription initiation site, 2) an expression vector should have the gene operons for expression switching, 3) an expression vector should have a ribosome binding site, and 4) an expression vector should have transcription and translation termination sites, all of which can improve stability of the transcription and translation products. The expression vectors recommended for protein A expression are pET (Novagen), pQE30 (Qiagen), PGS21a (genscript), pGAPZa A (Invitrogen), etc., in corresponding, the host cells which could be used for protein A expression are genetically engineered *Escherichia coli* (*E. coli*) or *Pichia pastoris* yeast strains. The host cells can express protein A on membranes or extracellularly.

According to different needs, those Protein A and/or their mutants could be isolated and purified using their physical and/or chemical properties. Usually those isolation and purification methods are protein precipitation (salting out), centrifugation, osmotic pressure shock, sonication, ultrafiltration, gel filtration, adsorption chromatography, ion exchange chromatography, affinity chromatography, high performance liquid chromatography or other liquid chromatography, dialysis etc., and the combination of these methods. Furthermore, target proteins fused with an affinity tag can be isolated and purified by affinity purification. Affinity tags described herein are, e.g., poly-histidine tag and FLAG® tag, which could be used for purification of protein A.

The binding affinity of protein A toward immunoglobulin can be measured by ELISA assay. For example, Protein A was immobilized on a solid phase carrier (here for example: a plate), free Protein A which was not immobilized on the carrier was washed out. And then an enzyme-labeled immunoglobulin was added and incubated for a certain time to allow efficient Protein A binding. By washing the solid phase carrier, free immunoglobulin which did not bind with immobilized protein A and other substances in liquid phase were removed from immunoglobulin-Protein A complexes which were immobilized on the solid phase carrier. Usually, the ratio of the amount of the enzyme-labeled immunoglobulin to the amount of immobilized Protein A in such a complex is 1:1. After adding chromogenic substrate, the substrate was catalyzed by the enzyme which bound to the immunoglobulin into colored product, and then the amount of immunoglobulin which bound to Protein A could be qualified and quantified by analyzing depth of coloration.

The alkali resistance and the chemical stability of these proteins can be easily confirmed by a person with technical expertise in this field. For example, proteins having been soaked in 0.5M NaOH for at least 60 hours are measured for immunoglobulin binding activity according to the ELISA assay described above. If the proteins having been treated by alkaline solutions can still maintain good binding activity, then these proteins are stable in an alkali environment. Another example is using an amino group or carboxyl group of the proteins to couple the proteins onto a solid phase carrier (here for example: SEPHAROSE® 4B) by diepoxide, epichlorohydrin, cyanogen bromide, N-hydroxysuccinimide and other coupling agents, which is packed into a chromatography column. The following steps (1 to 4) are performed as a cycle: 1) The column was loaded with excessive immunoglobulin molecules and then 2) washed with phosphate buffer at pH 8.0 thoroughly. 3) Immunoglobulin was eluted with glycine buffer at pH 3.0. 4) The elution was analyzed to determine the amount of total immunoglobulin that bound onto the column as binding capacity. The binding capacity was recorded after each cycle. In between each cycle, one step of Clean-In-Place (CIP) was done using alkali solution that was consisted of 0.5M NaOH and the column was regenerated and equilibrated with proper buffers. After 100 cycles, if the total binding capacity is not reduced, which means such proteins are very stable in the alkali environment. The proteins are very suitable for affinity purification process of immunoglobulins as affinity ligands.

Protein a Multimers which Contains Two or More Repetitive Units

The proteins discussed above are monomer. However, these proteins can be linked to form multimeric proteins, such as dimer, trimer, tetramer and others alike. Therefore, monomeric Protein A proteins described above are belong to the present invention and multimeric Protein A proteins which are formed by one kind protein of itself or the combinations of all other kinds Protein A proteins described above are also belong to the present invention. The multimeric protein A of the invention contain a linker unit which is composed of 4 to 10 optimized amino acids. This linker unit does not change the conformation or tertiary structure of Protein A, which makes multimeric Protein A sufficiently stable in the same alkaline environment as monomeric Protein A does. So the linker will not jeopardize the alkali resistance characteristics of the Protein A. In the present implementation of application, polymer is the dimer of Protein A, which is connected by a linker containing 4 amino acids (ADGK; SEQ ID NO: 56).

The present invention includes nucleic acid sequences encoding the above proteins and the sequences of the above Protein A multimers. The nucleic acid sequences were codon-optimized to avoid rare codons and the formation of secondary structures of mRNAs, the genes were synthesized using overlapping primers.

This invention includes such Protein A or Protein A multimer derivatives of which the N-terminal, C-terminal or side chain groups that have been chemically modified, such as acylation at the N-terminal amino group or esterification at the C-terminal carboxyl group, and those derivatives can tightly bind immunoglobulin. Modifications on a protein will play important roll on regulating protein's pI, stability, solubility, reactivity and biological activity. If providing a cysteine residue to the C-terminal of Protein A, then the protein could be coupled to a solid phase carrier with a thioether bond through this provided cysteine. This coupling method is easy to be applied with standard techniques and equipments.

Applications using Protein A, Protein A multimers or their derivatives as described above in isolation, purification or detection procedures of immunoglobulin.

Applications using genes of protein A, protein A multimers or their derivatives as described above in isolation, purification or detection procedures of immunoglobulin.

Commercial applications using the proteins described above include purification and detection of immunoglobulin. Applications for the immunoglobulin purification include affinity chromatographic separation methods, wherein at least one of the target molecules is separated from the matrix by binding to protein A or protein A multimers as described above. Specific steps involved are: 1) sample solution containing immunoglobulin is loaded through the protein A chromatography medium. In this step, components in the sample solution other than immunoglobulin will flow through unhindered, but immunoglobulin will be adsorbed onto the chromatographic medium. 2) Wash the medium with proper buffer (e.g., phosphate buffer) to remove non-specifically bound residual impurities. As discussed above, an alkaline solution could be used here if necessary. 3) Elute immunoglobulin from the medium with elution buffer. Usually immunoglobulin can be eluted by changing the elution pH, ionic strength of the buffer or by adding the competitive binding substances against protein A. The applications for detection of immunoglobulin include 1) Label or mark Protein A, Protein A mulitmers or their derivatives with an enzyme, chemiluminescent or isotope reagent, 2) Incubate labeled Protein A with the samples needed to be detected, 3) By analyzing protein A to detect immunoglobulin, which makes detection of immunoglobulin visualized.

Beneficial Effects (Benefits)

The present invention provides protein A, multimeric protein A and their derivatives which can be firmly bonded to regions of an immunoglobulin molecule other than the complementarity determining region, and also can be coupled to a solid phase carrier as ligands for isolation of immunoglobulin. This kind of protein A can maintain its chemical stability in an alkaline environment with pH 13-14, which enable the Protein A much more tolerant to the harsh condition that is used in Cleaning-In-Place (CIP) procedure. Therefore, the invention of protein A, its multimers and derivatives can be used in the purification and/or detection of immunoglobulin.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
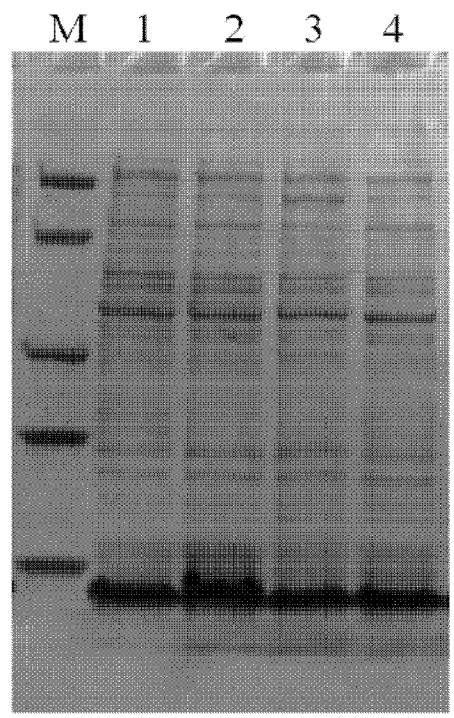
FIG. 1 shows expression of protein A in *Escherichia coli* detected by SDS-PAGE, wherein lane M is a Protein Marker (Genscript 94KD, 66 kD, 36KD, 25KD, 14KD), lanes 1 to 4 are expression of protein A in different *Escherichia coli* colonies.

Example 1: Construction of Vector Containing a Gene which is Encoding Protein A Fused with 6 Histidine Residues at its N-Terminus According to the codon preference of *E. coli* and to avoid secondary structure formation of mRNA, gene sequences of protein A fused with 6 histidine residues at its N-terminus were designed and optimized, which are shown here as SEQ ID NO:4 and SEQ ID NO:6 respectively; the corresponding amino acid sequences are shown as SEQ ID NO:3 and SEQ ID NO:5 respectively, of which the former is called protein A1 and the latter is called protein A2 in the following description. Using gene design software, multiple small gene fragments with certain length of overlapping sequences and similar annealing temperature were designed. All the small genes pieced together would cover the whole length of protein A1/A2 genes. The primer pairs were designed and synthesized according to those small gene sequences, of which the sequences were shown as here: Primers 4-1 to 4-8 (SEQ ID NOs: 16-23, respectively) are for the Protein A1 and Primers 6-1 to 6-8 (SEQ ID NOs: 24-31, respectively)

are for the Protein A2. Two rounds of PCR reactions were done to synthesize the genes. For the 1st round PCR, all the primers 4-1 to 4-8 or primers 6-1 to 6-8 were mixed together as primers and templates, PBO polymerase (Genscript Corporation) was used for PCR reaction. All PCR reactions were done with 2720 thermal cycler (Applied Biosystems) using the following method: the reaction cycles were 95° C. for 20 s, 55° C. for 20 s, 72° C. for 20 s, after a total of 25 cycles, one extension step was taken at 72° C. for 3 minutes, the PCR solutions were cooled down to 4° C. and stored as the 1st PCR products. These 1st PCR products were used as templates for the 2nd round. Respectively, forwarding primers (primer 4-1/primer 6-1) and reversing primers (primer 4-8/primer 6-8) were used in the 2nd PCR reaction to amplify whole genes of Protein A1/A2 with the same PCR method as described above. The PCR products from the 2nd round PCR reactions were loading to an agarose gel containing 1% ethidium bromide and purified by electrophoresis. The DNA bands were visualized under UV light and cut out from the gel. The amplified DNA fragments were purified using Quick Gel Extraction Kit (Genscript Corporation) and the protocol provided by the manufacturer. The purified DNA fragments were sequenced using ABI PRISM® BIGDYE® Terminator Cycle Sequencing Ready Reaction Kit and 3730×196-capillary DNA analyzer from Applied Biosystems Inc.

respectively. The PCR products were purified by agarose gel electrophoresis. Using CLONEEZ® cloning kit (Genscript Corporation) and following the kit instruction, gene fragments encoding protein A1/A2 were subcloned into pET15b vectors. Vectors containing protein A1/A2 genes were verified by DNA sequencing and named by the following abbreviation: vector containing gene encoding protein A1 with the amino acid sequence shown as SEQ ID NO:3 was named PET15b-ProteinA1; vector containing gene encoding protein A2 with the amino acid sequence shown as SEQ ID NO:5 was named PET15b-ProteinA2.

Example 2 Construction of Vector Containing a Gene which is Encoding Protein A Dimer Fused with 6 Histidine Residues at its N-Terminus According to the codon preference of *E. coli* and to avoid secondary structure formation of mRNA, gene sequences of protein A dimer fused with 6 histidine residues at its N-terminus were designed and optimized, which are shown here as SEQ ID NO:11 and SEQ ID NO:13 respectively; the corresponding amino acid sequences are shown as SEQ ID NO:10 and SEQ ID NO:12 respectively, of which the former is called protein AA1 and the latter is called protein AA2 for the following description. Using gene design software, multiple small gene fragments with certain length of overlap-

TABLE 1

PCR Primers for synthesizing Protein A1 and Protein A2 genes.

PCR Primers for synthesizing Protein A1 gene
(SEQ ID NOs: 16-23)

Primer 4-1  CCATGGGCTCACATCATCATCATCATCACGGCTCGGGTGCGGACGGTAA

Primer 4-2  ACGCATTCTGCTGTTCTTTTTCAAATTTACCGTCCGCACCC

Primer 4-3  AGAACAGCAGAATGCGTTCTACGAAATTCTGCATCTGCCGA

Primer 4-4  CATTACGCTGTTCTTCGGTCAGGTTCGGCAGATGCAGAATT

Primer 4-5  CCGAAGAACAGCGTAATGCATTTATCCAGTCTCTGAAAGATGATCCGAGC

Primer 4-6  ACCCAGCACGTTCGTAGACTGGCTCGGATCATCTTTCAGA

Primer 4-7  TACGAACGTGCTGGGTGAAGCGAAAAAACTGAACGATGCG

Primer 4-8  CATATGTCATTTCGGGGCCTGCGCATCGTTCAGTTTTTTC

PCR Primers for synthesizing Protein A2 gene
(SEQ ID NOs: 24-31)

Primer 6-1  CCATGGGCTCGCACCACCACCACCACCACGGCTCGGGCGCAGATGGCAAG

Primer 6-2  ATGCGTTCTGTTGTTCTTTTTCAAACTTGCCATCTGCGCC

Primer 6-3  AAAGAACAACAGAACGCATTCTACGAAATCCTGCATCTGCCGA

Primer 6-4  TGCGTTACGCTGTTCTTCGGTCAGGTTCGGCAGATGCAGGA

Primer 6-5  AGAACAGCGTAACGCATTCATCAAGTCTATCCGCGATGATCCG

Primer 6-6  CCCAGCACGTTCGTAGACTGGCTCGGATCATCGCGGATAG

Primer 6-7  CTACGAACGTGCTGGGCGAAGCGAAAAAACTGAATGATGC

Primer 6-8  CATATGTCATTTCGGGGCCTGCGCATCATTCAGTTTTTTCGC

DNA fragments which the sequences had been verified were used as templates for protein A1/A2 subcloning. Primer 7 (SEQ ID NO:7) with primer 8 (SEQ ID NO:8) or primers 7 (SEQ ID NO:7) with primer 9 (SEQ ID NO:9) were used amplify cDNA fragments of the protein A1 or A2 ping sequences and similar annealing temperature were designed. All the small genes pieced together would cover the whole length of protein AA1/AA2 genes. The primer pairs were designed and synthesized according to those small gene sequences, of which the sequences were shown as here: Primers 11-1 to 11-12 (SEQ ID NOs: 32-43) are for the Protein AA1 and Primers 13-1 to 13-12 (SEQ ID NOs: 44-55) are for the Protein AA2. Two rounds of PCR reactions were done to synthesize the genes. For the 1st round PCR, all the primers of 11-1 to 11-12 or primers 13-1 to 13-12 were mixed together as primers and templates, PBO polymerase (Genscript Corporation) was used for PCR reaction. All PCR reactions were done with 2720 thermal cycler (Applied Biosysytems) using the following method: the reaction cycles were 95° C. for 20 s, 55° C. for 20 s, 72° C. for 20 s, after a total of 25 cycles, one extension step was taken at 72° C. for 3 minutes, the PCR solutions was cooled down to 4° C. and stored as the 1st PCR products. These 1st PCR products were used as templates for the 2nd round.

Respectively, forwarding primers (primer 11-1/primer 13-1) and reversing primers (primer 11-12/primer 13-12) were used in the 2nd PCR reaction to amplify whole genes of Protein AA1/AA2 with the same PCR method as described above. The PCR products from the 2nd round PCR reactions were loading to an agarose gel containing 1% ethidium bromide and purified by electrophoresis. The DNA bands were visualized under UV light and cut out from the gel. The amplified DNA fragments were purified using Quick Gel Extraction Kit (Genscript Corporation) and the protocol provided by the manufacture. The purified DNA fragments were sequenced using ABI PRISM® BIGDYE® Terminator Cycle Sequencing Ready Reaction Kit and 3730×196-capillary DNA analyzer from Applied Biosystems Inc.

TABLE 2

PCR Primers for synthesizing Protein AA1 dimer and Protein AA2 dimer

PCR Primers for synthesizing Protein AA1 dimer gene (SEQ ID NOs: 32-43)

| | |
|---|---|
| Primer 11-1 | CCATGGGCTCACATCATCATCATCATCACGGCTCGGGTGCGGACGGTAA |
| Primer 11-2 | ACGCATTCTGCTGTTCTTTTTCAAATTTACCGTCCGCACCC |
| Primer 11-3 | AGAACAGCAGAATGCGTTCTACGAAATTCTGCATCTGCCGAACCTGACC |
| Primer 11-4 | TCAGAGACTGGATAAATGCATTACGCTGTTCTTCGGTCAGGTTCGGCAG |
| Primer 11-5 | TGCATTTATCCAGTCTCTGAAAGATGATCCGAGCCAGTCTACGAACGTGC |
| Primer 11-6 | CCTGCGCATCGTTCAGTTTTTCGCTTCACCCAGCACGTTCGTAGACTGG |
| Primer 11-7 | TGAACGATGCGCAGGCCCCGAAAGCGGATGGCAAATTCGAAAAAG |
| Primer 11-8 | GCAGAATTTCATAGAAGGCGTTCTGCTGTTCTTTTTCGAATTTGCCATCC |
| Primer 11-9 | CGCCTTCTATGAAATTCTGCACCTGCCGAATCTGACGGAAGAACAGCGCA |
| Primer 11-10 | GCTCGGATCGTCTTTCAGGCTCTGGATGAACGCATTGCGCTGTTCTTCCG |
| Primer 11-11 | TGAAAGACGATCCGAGCCAGTCCACGAATGTTCTGGGCGAAGCGAAAAA |
| Primer 11-12 | CATATGTCATTTCGGTGCTTGTGCGTCATTCAGTTTTTTCGCTTCGCCCA |

PCR Primers for synthesizing Protein AA2 dimer gene (SEQ ID NOs: 44-55)

| | |
|---|---|
| Primer 13-1 | CCATGGGCTCGCACCACCACCACCACCACGGCTCGGGCGCAGATGGCAAG |
| Primer 13-2 | TCGTAGAATGCGTTCTGTTGTTCTTTTTCAAACTTGCCATCTGCGCC |
| Primer 13-3 | ACAGAACGCATTCTACGAAATCCTGCATCTGCCGAACCTGACCGA |
| Primer 13-4 | CGCGGATAGACTTGATGAATGCGTTACGCTGTTCTTCGGTCAGGTTCGGC |
| Primer 13-5 | TCATCAAGTCTATCCGCGATGATCCGAGCCAGTCTACGAACGTGCTGGG |
| Primer 13-6 | GGCCTGCGCATCATTCAGTTTTTTCGCTTCGCCCAGCACGTTCGTAG |
| Primer 13-7 | AATGATGCGCAGGCCCCGAAAGCGGATGGTAAATTTGAAAAAGAACAGCA |
| Primer 13-8 | AGGTGCAGAATTTCATAGAAGGCGTTCTGCTGTTCTTTTTCAAATTTACC |
| Primer 13-9 | CTTCTATGAAATTCTGCACCTGCCGAATCTGACGGAAGAACAGCGTAATG |
| Primer 13-10 | GCTCGGATCGTCACGAATGCTTTTAATGAACGCATTACGCTGTTCTTCCG |
| Primer 13-11 | CGTGACGATCCGAGCCAGAGCACGAATGTCCTGGGCGAAGCCAAAAA |
| Primer 13-12 | CATATGTCATTTCGGTGCTTGTGCGTCGTTCAGTTTTTTGGCTTCGCCCA |

DNA fragments which the sequences had been verified were used as templates for protein AA1/AA2 subcloning. Primer 7 (SEQ ID NO:7) with primer 14 (SEQ ID NO:14) or primers 7 (SEQ ID NO:7) with primer 15 (SEQ ID NO:15) were used amplify cDNA fragments of the protein AA1 or AA2 respectively. The PCR products were purified by agarose gel electrophoresis. Using CLONEEZ® cloning kit (Genscript Corporation) and following the kit instruction, gene fragments encoding protein AA1/AA2 were subcloned into pET15b vectors. Vectors containing protein AA1/AA2 genes were verified by DNA sequencing and named by the following abbreviation: vector containing gene encoding protein AA1 with the amino acid sequence shown as SEQ ID NO:10 was named PET15b-ProteinAA1; vector containing gene encoding protein AA2 with the amino acid sequence shown as SEQ ID NO:12 was named PET15b-ProteinA2.

Example 3 Expression of Protein A with N-Terminal Fused Six Histidine Residues

The plasmid PET15b-ProteinA1 was transformed into competent cells of *Escherichia coli* strain BL21. *Escherichia coli* BL21 containing the plasmid PET15b-ProteinA1 was inoculated into the culture broth (1 g/L peptone, 5 g/L yeast extract, 5 g/L NaCl, and 100 mg/L Ampicillin) and cultured at 37° C. When cells reached the logarithmic growth curve, 0.5 mM IPTG was added into the broth to induce protein expression for 4 hours, cell pellets were collected by centrifugation. A small amount of the cell was heated at high temperature (95° C.) and the whole cell lysate was loaded onto 4~20% gradient SDS-PAGE gel for analysis. As shown in FIG. 1, a clear band was detected around 7~8KD which was protein A.

Figure 2:
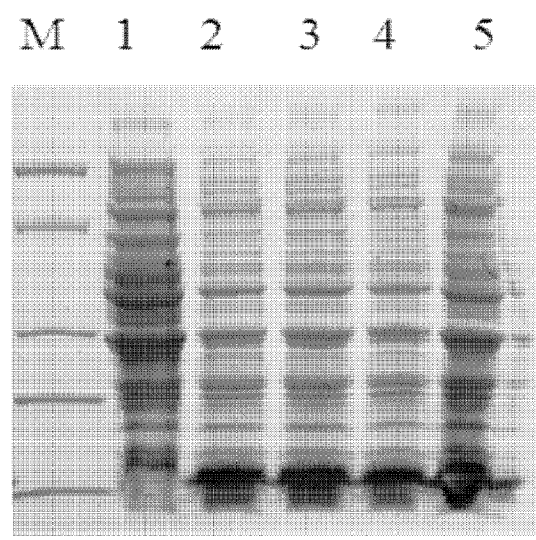
FIG. 2 shows expression of protein A dimer in *Escherichia coli* detected by SDS-PAGE, wherein lane M is a Protein Marker (Genscript 94KD, 66 kD, 36KD, 25KD, 14KD), lanes 1 to 4 are expression of the protein A dimer in different *Escherichia coli* colonies.

Example 4 Expression of Protein A Dimer with N-Terminal Fused Six Histidine Residues The plasmid PET15b-ProteinAA1 was transformed into competent cells of *Escherichia coli* BL21. *Escherichia coli* BL21 containing the plasmid PET15b-Protein AA1 was inoculated into the culture broth (1 g/L peptone, 5 g/L yeast extract, 5 g/L NaCl, and 100 mg/L Ampicillin) and cultured at 37° C., when cells reached their logarithmic growth curve 0.5 mM IPTG was added to induce protein expression for 4 hours. Cell pellets were collected by centrifugation. A small amount of bacteria was heated at high temperature (95° C.) and the whole cell lysate was loaded onto 4~20% gradient SDS-PAGE gel for analysis. As shown in FIG. 2, a clear band was detected around 14~15KD which was protein A dimer.

Figure 3:
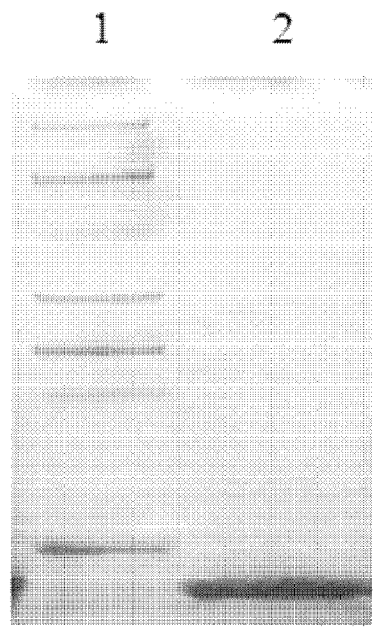
FIG. 3 is an image of SDS-PAGE; Protein A was purified by Ni column, wherein lane 1 is Protein Marker (Genscript 94KD, 66 kD, 36KD, 25KD, 14KD), lane 2 is protein A elution.

Example 5 Purification of Protein A with the N-Terminal Fused Six Histidine Residues The constant flow pump was rinsed with distilled water, and then the empty glass chromatographic column. About 200 ml Ni-IDA resin (Genscript Corporate) was packed into the column. Using the constant flow pump, the column was equilibrated with equilibration buffer (20 mM Tris 300 mM NaCl) for about 3 L (20CV) at the flow rate of 5 ml/min. 10 g cell pellets expressing protein A1 were suspended with 200 ml equilibration buffer (20 mMTris 300NaCl) and sonicated (Ningbo Xinzhi bio technology limited company JY98 IIIDH). Cell lysate was centrifuged and the supernatant was loaded onto the Ni-IDA column at the flow rate of 2 ml/min. Then the column was excessively washed with equilibration buffer at the flow rate of 5 ml/min to remove unbounded proteins and contaminants until the UV being stable. Then the target protein was eluted with elution buffer (20 mM Tris, 300 mMNaCl, 250 mM Iminazole) at the flow rate of 5 ml/min and collected. The eluted protein was loaded onto 4~20% gradient SDS-PAGE for analysis. As shown in FIG. 3, the purity of protein A after Ni-IDA column was above 90%.

Figure 4:
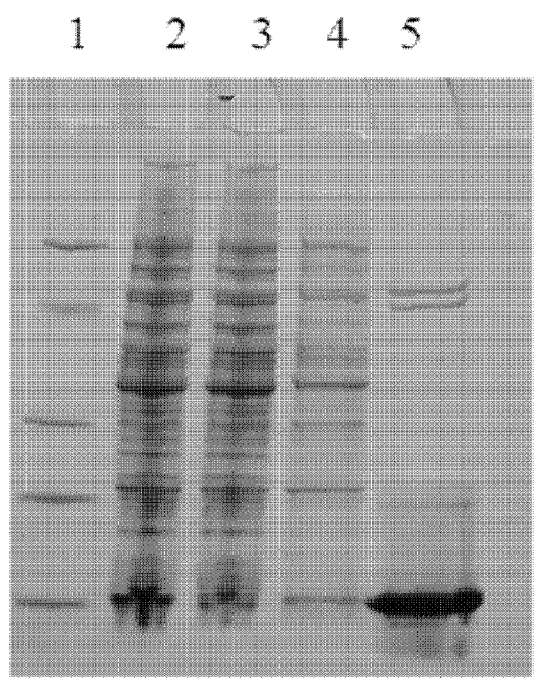
FIG. 4 is an image of SDS-PAGE; Protein A dimer was purified by Ni column, wherein lane 1 is Protein Marker (Genscript 94KD, 66 kD, 36KD, 25KD, 14KD), lane 2 is cell lysate supernatant, lane 3 is flow-through, lane 4 is protein A dimer eluted by the equilibration buffer, lane 5 is protein A dimer elution.

Example 6 Purification of Protein A Dimer with the N-Terminal Fused Six Histidine Residues The constant flow pump was rinsed with distilled water, and then the empty glass chromatographic column. About 200 ml Ni-IDA resin (Genscript Corporate) was packed into the column. Using the constant flow pump, the column was equilibrated with equilibration buffer (20 mM Tris 300 mMNaCl) for about 3 L (20CV) at the flow rate of 5 ml/min. 10 g cell pellets expressing protein A1 were suspended with 200 ml equilibration buffer (20 mMTris 300NaCl) and sonicated (Ningbo Xinzhi bio technology limited company JY98 IIIDH). Cell lysate was centrifuged and the supernatant was loaded onto the Ni-IDA column at the flow rate of 2 ml/min. Then the column was excessively washed with equilibration buffer at the flow rate of 5 ml/min to remove unbounded proteins and contaminants until the UV being stable. Then the target protein was eluted with elution buffer (20 mM Tris, 300 mMNaCl, 250 mM Imidazole) at the flow rate of 5 ml/min and collected. The eluted protein was loaded onto 4~20% gradient SDS-PAGE for analysis. As shown in FIG. 4, the purity of protein A after Ni-IDA column was above 90%.

7 Protein a or Protein A Dimer with the N-Terminal Fused Six Histidine Residues Used as an Ligand for Affinity Chromatographic Medium to Purify Immunoglobulin Using the amino group, protein A or protein A dimer with the N-terminal fused six histidine residues were coupled onto the epoxy-based surface of agarose medium to make affinity chromatographic resin. Here 10 mg dimeric protein A or protein A was coupled to an epoxy-based surface of 1 ml SEPHAROSE® 4B (GE Healthcare) agarose beads to make Protein A affinity resin, of which 0.5 ml resin was used for immunoglobulin purification test. Firstly, the constant flow pump was cleaned with 20 ml double distilled water, then the empty chromatographic column was cleaned. 0.5 ml resin was packed into the column. Using constant flow pump the column was equilibrated with 10 ml phosphate buffer (containing 0.15M NaCl, 30 mM Na2HPO4, 10 mM NaH2PO4 pH 7) at the flow rate of 1 ml/min.

Figure 5:
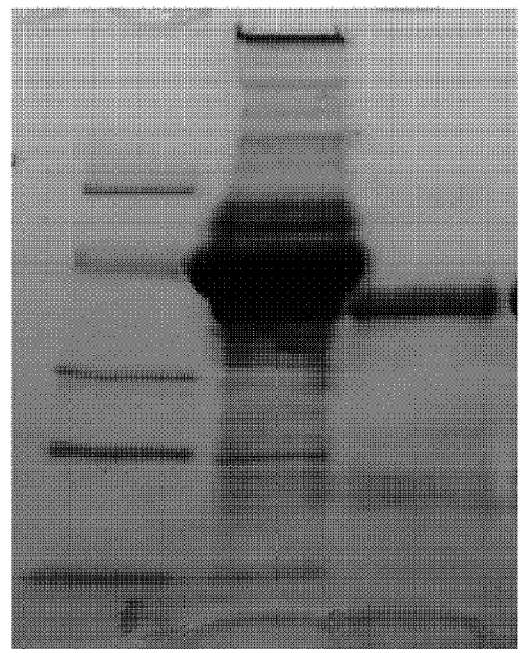
FIG. 5 is an image of SDS-PAGE; Protein A as an affinity ligand to purify immunoglobulin from human serum, wherein lane 1 is Protein Marker (Genscript 94KD, 66 kD, 36KD, 25KD, 14KD), lane 2 is human serum, lane 3 is purified human immunoglobulin using protein A as ligand for affinity chromatography.
Figure 6:
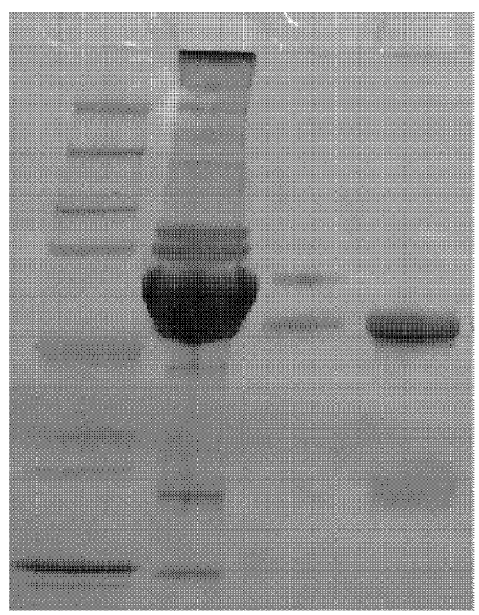
FIG. 6 is an image of SDS-PAGE; Protein A dimer as an affinity ligand to purify immunoglobulin from human serum, where lane 1 is Protein Marker (Genscript Corporation) 220KD, 150KD, 100KD, 75KD, 50KD, 35 kD, 25 kD, 15KD), Lane 2 is human serum, lane 3 is proteins eluted by washing buffer (phosphate buffer), lane 4 is purified human immunoglobulin using protein A dimer as ligand for affinity chromatography.

15 ml of human serum at the concentration of 5 mg/ml was used as testing sample and loaded to the packed column at the flow rate of 0.5-1 ml/min to the saturate the binding of immunoglobulin to the protein A ligands, and then washed the column with 20 ml (40CV) phosphate buffer (containing 0.15M of NaCl, 30 mM Na2HPO4, 10 mMNaH2PO4 pH 7.0) to remove unbound proteins and contaminants. Human immunoglobulin was finally eluted with 0.1M pH 3.0 glycine buffer and collected with UV detection. 20 uL of the eluted fraction was loaded onto 4-20% gradient SDS-PAGE gel for analysis. As shown in FIGS. 5 and 6, protein A or protein A dimer can isolate immunoglobulin with high purity from the serum.

Figure 7:
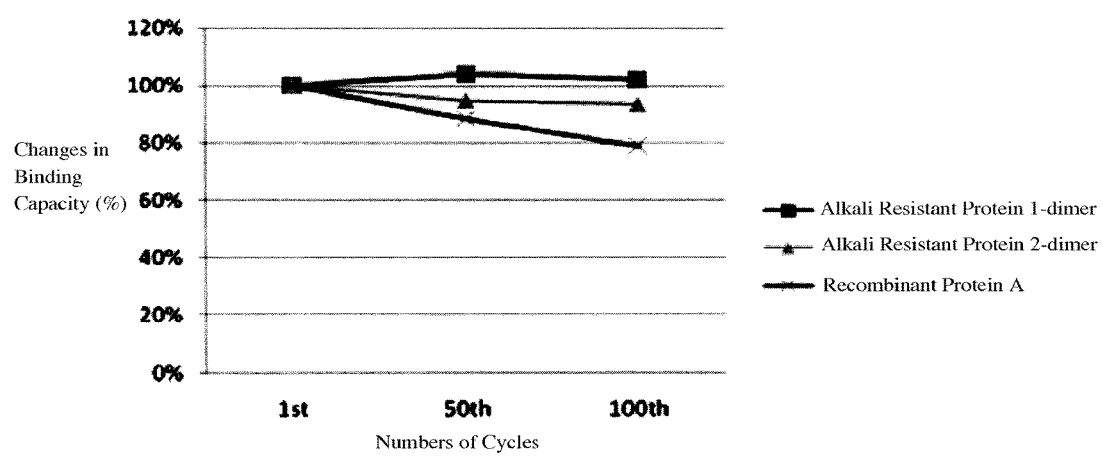
FIG. 7 shows alkali resistance tests for Protein A dimer as an affinity ligand.

Example 8 Alkali Resistance Tests of Protein a or Protein A Dimer with the N-Terminal Fused Six Histidine Residues as Ligands of Affinity Chromatographic Medium for Purifying Immunoglobulin 0.5 ml of SEPHAROSE® beads conjugated protein A dimer with six N-terminal histidine residues was used for Clean-In-Place (CIP) test using alkaline solutions. First, the procedure of Example 7 was performed, and the total amount of eluted immunoglobulin was calculated as column capacity. After elution, CIP was performed using 15 ml 0.5M NaOH solution at a flow rate of 1 ml/min to clean the resin thoroughly. And then followed with 10 ml of phosphate buffer (containing 0.15M of NaCl, 30 mMNa2HPO4, 10 mM NaH2PO4 adjusted to pH 7.0) at the same flow rate to wash out NaOH and re-equilibrate the column. Another procedure of Example 7 was performed to determine the binding capacity of the column, which could be used as binding ability of protein A ligand to immunoglobulin. As shown in FIG. 7, after 100 cycles of CIP with alkaline solution, the protein A dimer used as an affinity chromatographic ligand still remained good binding ability to immunoglobulin.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A multimer of a recombinantly expressed mutant protein A molecule comprising at least two recombinant expressed mutant protein A molecules for isolating, purifying, or detecting an immunoglobulin, the mutant protein A molecule comprising the amino acid sequence of SEQ ID NO:1, the amino acid sequence of SEQ ID NO:2, the amino acid sequence of residues 7 to 54 of SEQ ID NO:1, or the amino acid sequence of residues 7 to 54 of SEQ ID NO:2.

2. The multimer of claim 1, wherein the mutant protein A molecule is stable under alkaline conditions of pH 13-14.

3. The multimer of claim 1, wherein the at least two recombinantly expressed mutant protein A molecules comprise the same amino acid sequence.

4. The multimer of claim 3, wherein the multimer is a dimer, trimer, or tetramer comprising two, three, or four protein A mutants, respectively.

5. The multimer of claim 3, wherein the one or more protein A mutants are linked together via one or more linker units comprising 4 to 10 amino acids.

6. The multimer of claim 5, wherein the linker unit comprises the amino acid sequence ADGK (SEQ ID NO: 56).

7. The multimer of claim 3, further comprising six histidine residues fused to the N-terminal end of the multimer.

8. The multimer of claim 7, comprising the amino acid sequence of SEQ ID NO: 10 or SEQ ID NO: 12.

* * * * *